United States Patent
Abrahmsen (10) Patent No.: US 9,175,067 B2
(45) Date of Patent: Nov. 3, 2015

(54) IMMUNOGLOBULIN G FC REGION BINDING POLYPEPTIDE

(75) Inventor: Lars Abrahmsen, Bromma (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 205 days.

(21) Appl. No.: 13/583,686

(22) PCT Filed: Mar. 7, 2011

(86) PCT No.: PCT/EP2011/053362
§ 371 (c)(1),
(2), (4) Date: Oct. 11, 2012

(87) PCT Pub. No.: WO2011/110515
PCT Pub. Date: Sep. 15, 2011

(65) Prior Publication Data
US 2013/0203962 A1 Aug. 8, 2013

(30) Foreign Application Priority Data
Mar. 8, 2010 (EP) .................... 10155835

(51) Int. Cl.
| C07K 16/00 | (2006.01) |
| B01D 15/38 | (2006.01) |
| B01J 20/28 | (2006.01) |
| B01J 20/285 | (2006.01) |
| B01J 20/286 | (2006.01) |
| B01J 20/32 | (2006.01) |
| C07K 14/31 | (2006.01) |
| C07K 16/06 | (2006.01) |

(52) U.S. Cl.
CPC ............ *C07K 16/00* (2013.01); *B01D 15/3804* (2013.01); *B01J 20/285* (2013.01); *B01J 20/286* (2013.01); *B01J 20/28033* (2013.01); *B01J 20/3274* (2013.01); *C07K 14/31* (2013.01); *C07K 16/065* (2013.01); *B01D 15/3809* (2013.01)

(58) Field of Classification Search
None
See application file for complete search history.

(56) References Cited

U.S. PATENT DOCUMENTS

| 5,143,844 A | 9/1992 | Abrahmsen |
| 7,709,209 B2 * | 5/2010 | Hober et al. .................. 435/7.1 |
| 2005/0147962 A1 | 7/2005 | Wagstrom et al. |
| 2006/0194955 A1 | 8/2006 | Hober et al. |

FOREIGN PATENT DOCUMENTS

| WO | 2009080811 | 7/2009 |
| WO | 2009/146755 | 12/2009 |
| WO | WO 2009146755 A1 * | 12/2009 |

OTHER PUBLICATIONS

EP Office Action dated Nov. 14, 2013 issued on corresponding EP patent application No. 11707162.1.

(Continued)

*Primary Examiner* — Michael Szperka
(74) *Attorney, Agent, or Firm* — Parks Wood LLC (57) ABSTRACT

An immunoglobulin G Fc region binding polypeptide is provided, consisting of an amino acid sequence selected from i) a variant of Protein A domain or Protein Z and ii) an amino acid sequence which has at least 95% identity thereto. Also provided are methods for producing the polypeptide, compositions comprising the polypeptide, polynucleotides encoding the polypeptide, multimers of the polypeptide, and methods of using the polypeptide.

26 Claims, 4 Drawing Sheets

| SEQ ID NO: | Amino acid sequence |
|---|---|
| 1 | PAKFDKEQQ NAFYEILHLP NLTEEQRNAF IQKLKDEPSQ SAELLAEAKQ LNEAQAGCD |
| 2 | PAKFDKEQQ NAFYEILHLP TLTEEQRNAF IQKLKDEPSQ SAELLAEAKQ LDEAQAGCD |
| 3 | PAKFDKEQQ NAFYEILHLP NLTEEQRNAF IQKLKDEPSQ SAELLAEAKQ LNEAQAPK<br>AEAKFDKEQQ NAFYEILHLP NLTEEQRNAF IQKLKDEPSQ SAELLAEAKQ LNEAQAGCD |
| 4 | PAKFDKEQQ NAFYEILHLP TLTEEQRNAF IQKLKDEPSQ SAELLAEAKQ LDEAQAPK<br>AEAKFDKEQQ NAFYEILHLP TLTEEQRNAF IQKLKDEPSQ SAELLAEAKQ LDEAQAGCD |
| 5 | AEAKFDKEQQ NAFYEILHLP NLTEEQRNAF IQKLKDEPSQ SAELLAEAKQ LNEAQAPK<br>AEAKFDKEQQ NAFYEILHLP NLTEEQRNAF IQKLKDEPSQ SAELLAEAKQ LNEAQAGC |
| 6 | AEAKFDKEQQ NAFYEILHLP TLTEEQRNAF IQKLKDEPSQ SAELLAEAKQ LDEAQAPK<br>AEAKFDKEQQ NAFYEILHLP TLTEEQRNAF IQKLKDEPSQ SAELLAEAKQ LDEAQAGC |
| 7 | VDAKYAKEMR NAYWEIALLP NLTNQQKRAF IRKLYDDPSQ SSELLSEAKK LNDSQAPK |
| 8 | VDAKYAKEMR NAYWEIALLP NLTNQQKRAF IRKLYDEPSQ SSELLSEAKK LNDSQAPK |
| 9 | GSSHHHHHHL QSSGVDLGTD P<br>VDAKYAKEMR NAYWEIALLP NLTNQQKRAF IRKLYDEPSQ SSELLSEAKK LNDSQAPKVD |

(56) References Cited

OTHER PUBLICATIONS

Li, N., et al., Journal of Pharmaceutical and Biomedical Analysis, 50 (2009) 73-78.
Linhult, M., et al., Proteins: Structure, Function, and Bioinformatics, 55 (2004) 407-416.
Nilsson, B., et al., Protein Engineering, 1 (1987) 107-113.
Saito, A., et al., Protein Engineering, 2 (1989) 481-487.
Taverna, D., et al., Journal of Molecular Biology, 315 (2002) 479-484.

* cited by examiner

| SEQ ID NO: | Amino acid sequence |
|---|---|
| 1 | PAKFDKEQQ NAFYEILHLP NLTEEQRNAF IQKLKDEPSQ SAELLAEAKQ LNEAQAGCD |
| 2 | PAKFDKEQQ NAFYEILHLP TLTEEQRNAF IQKLKDEPSQ SAELLAEAKQ LDEAQAGCD |
| 3 | PAKFDKEQQ NAFYEILHLP NLTEEQRNAF IQKLKDEPSQ SAELLAEAKQ LNEAQAPK<br>AEAKFDKEQQ NAFYEILHLP NLTEEQRNAF IQKLKDEPSQ SAELLAEAKQ LNEAQAGCD |
| 4 | PAKFDKEQQ NAFYEILHLP TLTEEQRNAF IQKLKDEPSQ SAELLAEAKQ LDEAQAPK<br>AEAKFDKEQQ NAFYEILHLP TLTEEQRNAF IQKLKDEPSQ SAELLAEAKQ LDEAQAGCD |
| 5 | AEAKFDKEQQ NAFYEILHLP NLTEEQRNAF IQKLKDEPSQ SAELLAEAKQ LNEAQAPK<br>AEAKFDKEQQ NAFYEILHLP NLTEEQRNAF IQKLKDEPSQ SAELLAEAKQ LNEAQAGC |
| 6 | AEAKFDKEQQ NAFYEILHLP TLTEEQRNAF IQKLKDEPSQ SAELLAEAKQ LDEAQAPK<br>AEAKFDKEQQ NAFYEILHLP TLTEEQRNAF IQKLKDEPSQ SAELLAEAKQ LDEAQAGC |
| 7 | VDAKYAKEMR NAYWEIALLP NLTNQQKRAF IRKLYDDPSQ SSELLSEAKK LNDSQAPK |
| 8 | VDAKYAKEMR NAYWEIALLP NLTNQQKRAF IRKLYDEPSQ SSELLSEAKK LNDSQAPK |
| 9 | GSSHHHHHHL QSSGVDLGTD P<br>VDAKYAKEMR NAYWEIALLP NLTNQQKRAF IRKLYDEPSQ SSELLSEAKK LNDSQAPKVD |

IMMUNOGLOBULIN G FC REGION BINDING POLYPEPTIDE

CROSS-REFERENCE TO RELATED APPLICATIONS

This application is a filing under 35 U.S.C. 371 of international application number PCT/EP2011/053362, filed Mar. 7, 2011, published on Sep. 15, 2011 as WO 2011/110515, which claims priority to application number 10155835.1 filed in the European Patent Office on Mar. 8, 2010.

FIELD OF THE INVENTION

This invention relates to a polypeptide which binds to immunoglobulin G Fc (IgG Fc), and to methods for its production. The polypeptide has industrial application for example in separation and/or purification in the production of antibodies and/or Fc fusion proteins, e.g. in chromatography.

BACKGROUND

In the industrial production of monoclonal antibodies and Fc fusion proteins, purification is frequently carried out using chromatography. Protein A from *Staphylococcus aureus* has long been used as affinity ligand in such applications, due to the native affinity of Protein A for the Fc portion of IgG. Protein A in its entirety, as well as the five individual Fc-binding domains thereof, have subsequently served as starting points for the rational design of engineered affinity ligands with improved properties.

For example, the B domain of Protein A served as a starting point for the creation of the engineered, IgG Fc-binding, single-domain protein Z (Nilsson B et al, Protein Eng 1(2): 107-13, 1987). In order to improve the stability of this protein in alkaline conditions, such as those employed in cleaning-in-place procedures during industrial chromatographic processes, Linhult et al (Proteins 55(2):407-16, 2004) proposed a variant of protein Z comprising mutated asparagine residues. This variant was further developed by GE Healthcare, Uppsala, Sweden, into the commercial product MAbSelect™ SuRe. Additional Z variants with IgG Fc affinity are disclosed in WO2009/146755.

Mutated binding proteins based on protein Z, in which the native IgG Fc binding has been modified, are described in WO2009/080811.

Native Protein A, with its five individual IgG Fc-binding domains, has been shown to bind only 2 molecules of IgG, or 3 molecules of recombinant Fc-fragment, despite the fact that each of the five domains has the capacity to bind one IgG (Birger Jansson, PhD Thesis, Stockholm, Sweden, 1996, ISBN 91-7170-656-9).

Despite the comparable success of currently used IgG Fc affinity ligands, there is a continued need for improvement, especially with regard to the combined requirements of improving stoichiometry and at the same time maintaining, and ideally improving, stability towards acidic and alkaline conditions. The continued provision of agents with affinity for IgG Fc remains a matter of substantial interest.

SUMMARY OF THE INVENTION

According to a first aspect thereof, the invention provides an immunoglobulin G Fc (IgG Fc) binding polypeptide, comprising an amino acid sequence selected from:

i) $X_1$-([spacer1]-KFDKEQQN AFYEILX$_{17}$LPX$_{20}$ LTEEQRNAFI QKLKDX$_{36}$PSQS AELLAEAKQL X$_{51}$EAQA-[spacer2])$_n$-C$_{CTERM-1}$X$_{CTERM}$ (SEQ ID NO: 10)

wherein, independently of each other,
$X_1$ is P or nothing;
[spacer1] is an amino acid sequence consisting of 1-3 amino acid residues;
$X_{17}$ is any amino acid residue;
$X_{20}$ is any amino acid residue;
$X_{36}$ is any amino acid residue except for D;
$X_{51}$ is any amino acid residue;
[spacer2] is an amino acid sequence consisting of 0-20 amino acid residues;
$X_{CTERM}$ is D or nothing; and
n is 1-4;
and
ii) an amino acid sequence which has at least 95% identity to the sequence defined in i).

In an embodiment of this aspect of the invention, the immunoglobulin G Fc (IgG Fc) binding polypeptide consists of an amino acid sequence selected from i) and ii) as defined above.

The amino acid sequence of the polypeptide according to the invention has been conceived by the present inventor in order to provide an optimized IgG Fc-binding molecule, taking as the starting point the various domains of Protein A from *Staphylococcus* as well as protein Z, derived from the B domain of Protein A. Similar to the modular domain structure of natural Portein A or previously known engineered variants thereof, the polypeptide of the present invention provides one or more distinct domains possessing IgG Fc-binding capacity. In particular, the amino acid sequence between the two spacer sequences is predicted to fold into a single, three-helical bundle domain with IgG Fc-binding capacity. As described above, the number n may be between 1 and 4, signifying that a polypeptide according to the invention may have from one to four distinct IgG Fc-binding domains separated by the spacer sequences, making up a monomer, dimer, trimer or tetramer of such domains.

In protein Z, the amino acid position corresponding to position 17 in amino acid sequence i) above is occupied by a histidine residue. In the inventive polypeptide, $X_{17}$ may be H, but may also be substituted by any other amino acid residue. Substitution at this position may be motivated by the general need to avoid chemically reactive amino acids.

In protein Z, the amino acid position corresponding to position 36 in amino acid sequence i) above is occupied by an aspartic acid residue. In the amino acid sequence i), however, this position is substituted for example by a glutamic acid residue or an alanine residue. Without wishing to be bound by theory, this difference is presently thought to serve the two separate purposes of a) increasing the acid stability of the polypeptide and b) removing a DP dipeptide within the three-helix bundle domain, which would otherwise be susceptible to acid catalyzed cleavage. One aspect of the invention, described in more detail below, uses the susceptibility of the DP dipeptide motif in another part of the molecule, and the presence of a DP dipeptide at positions 36-37 would diminish the practicality of this aspect of the invention.

In protein Z, the amino acid position corresponding to position 49 in amino acid sequence i) above is occupied by a lysine residue. In the amino acid sequence i), however, this position is occupied by a glutamine residue.

As the skilled person will realize, the function of any polypeptide, such as the IgG Fc-binding capacity of the polypeptides according to the invention, is dependent on the tertiary structure of the polypeptide. It is possible to make changes to the sequence of amino acids in an a-helical polypeptide without affecting the function thereof (Taverna and Goldstein, J Mol Biol 315(3):479-84, 2002; He et al, Proc Natl Acad Sci USA 105(38):14412-17, 2008). Thus, the invention encompasses modified variants of i), which are such that the resulting sequence is at least 95% identical to a sequence belonging to the class defined by i). For example, it is possible that an amino acid residue belonging to a certain functional grouping of amino acid residues (e.g. hydrophobic, hydrophilic, polar etc) could be exchanged for another amino acid residue from the same functional group.

When reference is made herein to the degree of identity between the amino acid sequences of different polypeptides, the lower limit of 95% identity to a sequence disclosed herein is given. In some embodiments, the inventive polypeptide may have a sequence which is at least 96%, at least 97%, at least 98% or at least 99% identical to the sequence described herein. The term "% identity", as used throughout the specification and the appended claims, may for example be calculated as follows. The query sequence is aligned to the target sequence using the CLUSTAL W algorithm (Thompson, J. D., Higgins, D. G. and Gibson, T. J., Nucleic Acids Research, 22: 4673-4680 (1994)). A comparison is made over the window corresponding to the shortest of the aligned sequences. The shortest of the aligned sequences may in some instances be the target sequence, such as the 29 amino acid residue HER3 binding motif. In other instances, the query sequence may constitute the shortest of the aligned sequences. The query sequence may for example consist of at least 10 amino acid residues, such as at least 20 amino acid residues. The amino acid residues at each position are compared, and the percentage of positions in the query sequence that have identical correspondences in the target sequence is reported as % identity.

In one embodiment of the polypeptide according to the invention, [spacer1] is selected from A, AE and AEA. [spacer1] may for example be A.

In one embodiment of the polypeptide according to the invention, $X_{17}$ is H.

In one embodiment of the polypeptide according to the invention, $X_{20}$ is any amino acid residue except for N. $X_{20}$ may for example be T.

In an alternative embodiment, $X_{20}$ is N.

In one embodiment of the polypeptide according to the invention, $X_{36}$ is selected from E and A. $X_{36}$ may for example be E.

In one embodiment of the polypeptide according to the invention $X_{51}$ is any amino acid residue except for N. $X_{51}$ may for example be D.

In an alternative embodiment, $X_{51}$ is N.

In one embodiment of the polypeptide according to the invention, all amino acid residues of [spacer2] are independently selected from A, E, F, G, I, K, L, P, Q, R, S, T and V, in particular from A, E, G, K, P, Q, R, S and T, such as from G, Q and S. In an even more specific embodiment, [spacer2] is G.

As discussed above, n is a number between 1 and 4, i.e. it may be 1, 2, 3 or 4.

In polypeptides according to the invention wherein n>1, the multiple occurrences of [spacer1] may each individually consist of the same amino acid sequence or be different amino acid sequences. Likewise, in polypeptides according to the invention wherein n>1, the multiple occurrences of [spacer2] may each individually consist of the same amino acid sequence or be different amino acid sequences.

An IgG Fc-binding polypeptide according to any aspect of the invention may bind to IgG Fc such that the $K_D$ value of the interaction is at most $1\times10^{-6}$ M, for example at most $1\times10^{-7}$ M, such as at most $5\times10^{-8}$ M.

The polypeptide is advantageous in that it binds well to an IgG Fc. In particular, the polypeptide may be capable of binding to the Fc portion of a human IgG molecule. In some embodiments of the invention, the polypeptide is capable of binding to classes 1, 2 and 4 of human IgG, but not to class 3. In some embodiments, the polypeptide is capable of binding to the interface between the CH2 and CH3 domains of IgG Fc.

In one embodiment of the IgG Fc-binding polypeptide according to the invention, $X_1$ is P.

In one embodiment of the IgG Fc-binding polypeptide according to the invention, $X_{CTERM}$ is D.

In a particular embodiment of the IgG Fc-binding polypeptide according to the invention, $X_1$ is P and $X_{CTERM}$ is D.

Figure 1:
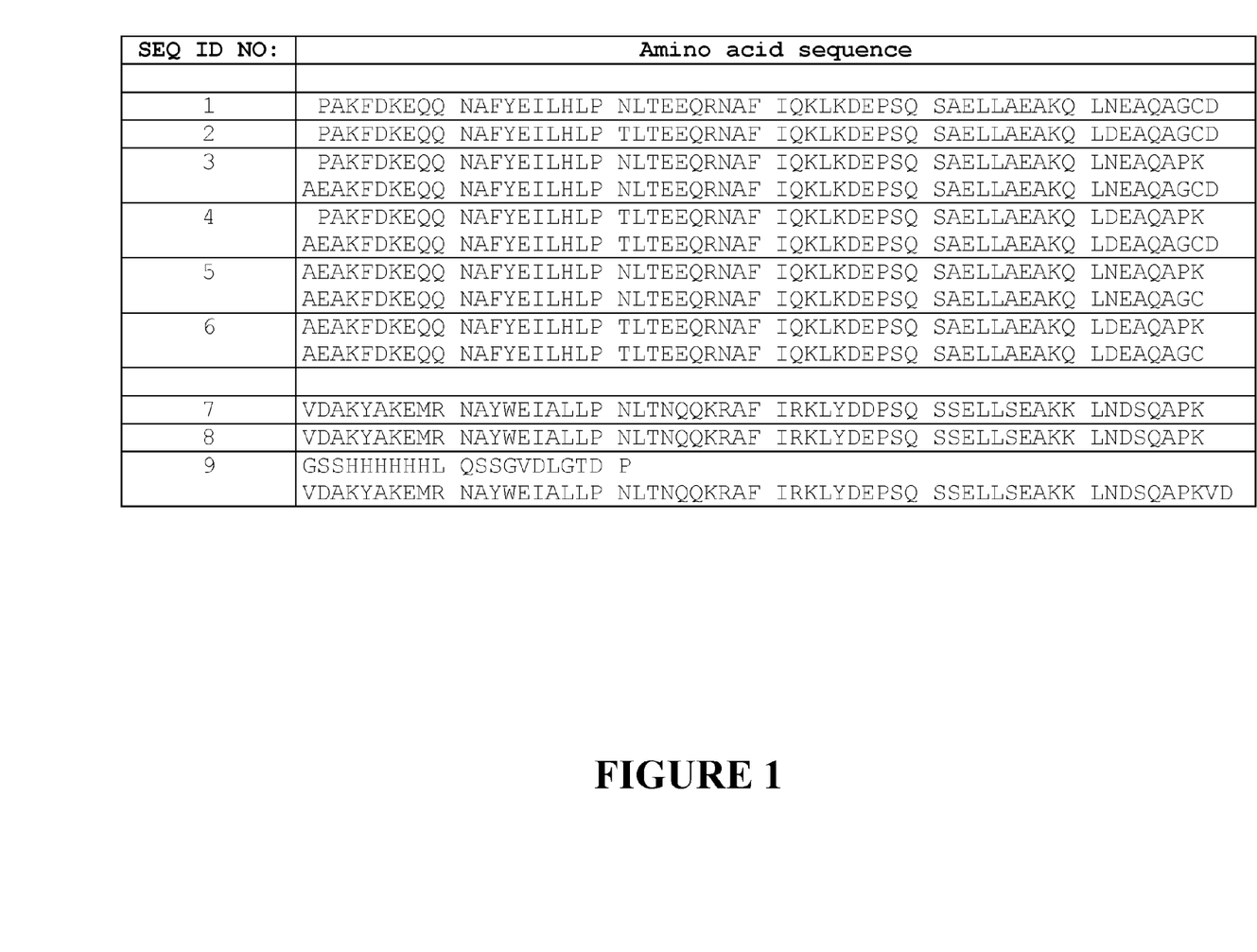
FIG. 1 is a table showing amino acid sequence information for polypeptides described herein. SEQ ID NO:1-6 are non-limiting examples of polypeptides according to the invention, whereas SEQ ID NO:7-9 are disclosed for illustrative and/or comparative purposes.

In one embodiment of the polypeptide according to the invention, the amino acid sequence i) is selected from SEQ ID NO:1-6 of the appended FIG. 1. It may for example be SEQ ID NO:1. As readily apparent, n=1 for the sequences SEQ ID NO:1-2, and n=2 for the sequences SEQ ID NO:3-6. It is also evident from the sequences themselves that SEQ ID NO:1-4 are examples of the embodiment in which $X_1$ is P and $X_{CTERM}$ is D, whereas SEQ ID NO:5-6 are examples of another embodiment.

In a related aspect, the invention provides a polynucleotide comprising a nucleotide sequence encoding any polypeptide according to the first aspect of the invention.

As explained above, in one embodiment of the polypeptide according to the first aspect of the invention, $X_1$ is P and $X_{CTERM}$ is D in the amino acid sequence thereof. This design of the N- and C-terminal amino acid residues enables a convenient approach to the production of the IgG Fc-binding polypeptide by recombinant DNA technology, by first producing a multimer having copies of the inventive polypeptide as subunits, each subunit being separated from the others via the dipeptide DP. The amino acid sequence DP is susceptible to acid catalyzed hydrolysis, so the dipeptide site between subunits may be used as a cleavage site for separation of the subunits in the multimer from each other. As non-limiting examples, the multimer may comprise 2-6 subunits, such as 4 subunits or 6 subunits. In this regard, it is pointed out that the subunits making up the multimer may themselves comprise from 1 to 4 distinct IgG Fc-binding domains, as disclosed above with regard to the number n in the sequence of i). The subunits separated by DP sequences and the single IgG Fc-binding domains may constitute the same structural elements in the multimer (i.e. if n=1), but may also constitute different structural elements of the construct (if n=2-4).

Thus, in a second aspect of the present invention, there is provided a multimer polypeptide comprising
  at least two subunits, each subunit being a polypeptide according to the first aspect wherein $X_1$ is P and $X_{CTERM}$ is D; and
  an N-terminal leader peptide comprising a D residue as the last residue thereof.

Thus, in order to provide a DP dipeptide suitable for cleavage, the N-terminal leader peptide has to comprise a D residue as the last residue thereof. In the multimer polypeptide, this D residue forms a DP dipeptide together with the $P_1$ residue of the first subunit. The exact sequence of the remainder of the N-terminal leader peptide is not critical for the invention, as long as any amino acid residue preceding the D residue does not interfere with cleavage of the DP dipeptide. The beginning of the leader peptide will depend on the expression system used for production. For example, intracellular expression may be used to yield a leader peptide of MD from which the M is then removed in vivo, from a soluble protein. If the expression is driven towards formation of inclusion bodies, a leader peptide of MXGD may be used, wherein X may be any amino acid or G or excluded.

The invention also provides a polynucleotide, which comprises a nucleotide sequence encoding a multimer polypeptide as described immediately above.

The present invention provides, in yet a related aspect, a method of producing a multimer polypeptide as described above, which method comprises:
  providing a host cell harboring an expression vector comprising a polynucleotide comprising a nucleotide sequence encoding a multimer as described above,
  culturing the host cell under conditions that enable the expression of said polynucleotide into a multimer polypeptide, and
  isolating the resulting multimer polypeptide.

Once the resulting multimer polypeptide has been isolated, it may be used as starting material for the production of the IgG Fc-binding polypeptides of the first aspect of the invention, since these polypeptides are present as the subunits of the multimer. Thus, the invention also provides a method of producing a polypeptide according to the first aspect, which method comprises:
  producing a multimer polypeptide using the method described immediately above,
  cleaving the multimer polypeptide at sites comprising the sequence DP using acid-catalyzed hydrolysis, yielding IgG Fc-binding polypeptides according to the first aspect of the invention and N-terminal leader peptide, and
  isolating said IgG Fc-binding polypeptides.

Whether or not they comprise DP sequences and whether or not they are prepared according to the convenient approach described in the previous section, any polypeptide according to the first aspect of the invention comprises a cysteine residue at the penultimate position $C_{CTERM-1}$ (which is in fact the ultimate position if $X_{CTERM}$ is not present). The incorporation of this cysteine residue into the amino acid sequence of the inventive polypeptide enables highly versatile chemical coupling of the polypeptide to other compounds. Using this cysteine residue to couple the polypeptide, directly or indirectly, to a matrix, enables the production of a separation medium useful for industrial-scale separation of IgG Fc-containing molecules, for example in a process for production of monoclonal antibodies. The affinity ligand in the separation medium or chromatography medium is the IgG Fc-binding polypeptide according to the first aspect of the invention. The matrix may be made from an organic or inorganic material. In one embodiment, the matrix is prepared from a native polymer, such as cross-linked carbohydrate material, e.g. agarose, agar, cellulose, dextran, chitosan, konjac, carrageenan, gellan, alginate etc. The native polymer matrices are easily prepared and optionally cross-linked according to standard methods, such as inverse suspension gelation (S Hjertén (1964), Biochim Biophys Acta 79(2):393-398). In an alternative embodiment, the matrix is prepared from a synthetic polymer or copolymer, such as cross-linked synthetic polymers, e.g. styrene or styrene derivatives, divinylbenzene, acrylamides, acrylate esters, methacrylate esters, vinyl esters, vinyl amides etc. Such synthetic polymer matrices are easily prepared and optionally cross-linked according to standard methods. As non-limiting examples of direct coupling to a matrix, the IgG Fc-binding polypeptide may be attached via $C_{CTERM-1}$ to a maleimide agarose, iodoacetyl sepharose or agarose, e.g. SulfoLink® from Pierce. As a non-limiting example of indirect coupling, the IgG Fc-binding polypeptide may be attached via $C_{CTERM-1}$ to a linker polymer, forming an intermediate, IgG Fc-binding composition. This intermediate composition may then in turn be coupled to a matrix via reactive groups in either the IgG Fc-binding polypeptide or in the linker polymer.

Preferred linker polymers are stable, both against acid and base catalyzed hydrolysis as well as against proteolytic degradation. They are hydrophilic, and of non-nucleic acid and non-peptidic origin. From a regulatory point of view, preferred polymers are those that have been previously used in vivo, but the invention is not limited thereto. A particularly preferred linker polymer is poly(ethylene glycol), PEG. The length of linker polymer between coupled IgG Fc-binding polypeptides should be sufficient to allow 1:1 stochiometry of the interaction between IgG Fc-containing molecules and each Fc-binding domain.

In the inventive IgG Fc-binding composition, the stability towards acid or base catalyzed hydrolysis is ensured by joining the folded domains using a chemically stable linker polymer.

Thus, in another aspect thereof, the invention provides an IgG Fc-binding composition, comprising at least one IgG Fc-binding polypeptide according to the first aspect, covalently coupled to a non-peptide, non-nucleic acid linker polymer via the cysteine residue $C_{CTERM-1}$.

In a related aspect, the invention provides a method of producing such an IgG Fc-binding composition. The method comprises:
  providing at least one IgG Fc-binding polypeptide according to the first aspect, and
  coupling said polypeptide to a non-peptide, non-nucleic acid linker polymer via the cysteine residue $C_{CTERM-1}$ present in said polypeptide.

The number of IgG Fc-binding polypeptides coupled to each molecule of polymer linker may be determined by design, for example by using a predetermined mixture of polymer molecules adapted for conjugation with different numbers of IgG Fc-binding polypeptides. For example, a polymer having 1-4 conjugation sites for IgG Fc-binding polypeptides may be used in the preparation of a homogeneous IgG Fc-binding composition, or a mixture of polymers having 1-4 conjugation sites may be used to prepare the corresponding Fc-binding composition.

In the case where the IgG Fc-binding polypeptide comprises the $P_1$ and $D_{CTERM}$ amino acid residues, the provision in the first step of this production method may be done according to the description above of a method of producing such polypeptides as subunits in a multimer, which subunits are separated by DP sequences amenable to cleavage by acid catalyzed hydrolysis. In other words, in this embodiment of the invention, a composition for use as affinity ligand in a chromatography medium may be prepared by i) expressing a multimer comprising the individual IgG Fc-binding polypeptides (whether mono-, di-, tri- or tetrameric) as subunits, ii) cleaving the multimer into its constituent subunits by acid catalyzed hydrolysis, iii) coupling the resulting subunits (i.e. the IgG Fc-binding polypeptides according to the invention) to the linker polymer via the $C_{CTERM-1}$ residue.

In some embodiments of the inventive composition and methods of producing it described above, the linker polymer is poly(ethylene glycol).

The composition according to the invention may suitably be connectable to a matrix or chromatography medium via the linker polymer. The chemical nature of the group used for attachment of the composition to the matrix is preferably different from that of the group used for conjugation of the IgG Fc-binding polypeptides to the linker polymer. Thanks to the stability of the IgG Fc-binding polypeptides according to the invention with regard to both acidic and basic conditions, activation of a reacting group may be done either by base or acid. The length of polymer between the matrix and the most proximal IgG Fc-binding polypeptide should not interfere with IgG binding properties of this domain. The choice between available coupling chemistries and adaptation of them to the present invention is within the abilities of the skilled person.

The terms "IgG Fc-binding" and "binding affinity for IgG Fc" as used in this specification refers to a property of a polypeptide which may be tested for example by the use of surface plasmon resonance technology, such as in a Biacore instrument (GE Healthcare). For example as described in the examples below, IgG Fc-binding affinity may be tested in an experiment in which IgG Fc, or a fragment of IgG Fc, is immobilized on a sensor chip of the instrument, and the sample containing the polypeptide to be tested is passed over the chip. Alternatively, the polypeptide to be tested is immobilized on a sensor chip of the instrument, and a sample containing IgG Fc, or fragment thereof, is passed over the chip. The skilled person may then interpret the results obtained by such experiments to establish at least a qualitative measure of the binding affinity of the polypeptide for IgG Fc. If a quantitative measure is desired, for example to determine a $K_D$ value for the interaction, surface plasmon resonance methods may also be used. Binding values may for example be defined in a Biacore 2000 instrument (GE Healthcare). IgG Fc is immobilized on a sensor chip of the measurement, and samples of the polypeptide whose affinity is to be determined are prepared by serial dilution and injected in random order. $K_D$ values may then be calculated from the results using for example the 1:1 Langmuir binding model of the BIAevaluation 4.1 software provided by the instrument manufacturer.

Where amino acid substitutions are introduced, these should not affect the basic structure of the polypeptide. For example, the overall folding of the Cα backbone of the polypeptide can be essentially the same as that of a domain of Protein A, i.e. having the same elements of secondary structure in the same order. Thus, polypeptides having this basic structure will have CD spectra that are similar to that of a wild-type Protein A domain. The skilled addressee is aware of other parameters that may be relevant. The requirement of conserving the basic structure places restrictions on which positions of the amino acid sequence may be subject to substitution. For example, it is preferred that amino acid residues located on the surface of the polypeptide are substituted, whereas amino acid residues buried within the core of the polypeptide "three-helix bundle" should be kept constant in order to preserve the structural properties of the molecule. The same reasoning applies to fragments of polypeptides of the invention.

Thus, the invention also covers polypeptides and compositions in which the IgG Fc-binding polypeptide described above is present as an IgG Fc-binding domain to which additional amino acid residues have been added at either terminal. These additional amino acid residues may play a role in the binding of IgG Fc by the polypeptide, but may equally well serve other purposes, related for example to one or more of the production, purification, stabilization in vivo and/or in vitro, coupling or detection of the polypeptide. Such additional amino acid residues may comprise one or more amino acid residues added for the purpose of chemical coupling. Such additional amino acid residues may provide a "tag" for purification or detection of the polypeptide such as a $His_6$ tag or a "myc" (c-myc) tag or a "FLAG" tag for interaction with antibodies specific to the tag.

The present invention also covers IgG Fc-binding polypeptides in which an IgG Fc-binding polypeptide as described above is present as an IgG Fc-binding domain to which additional peptides or proteins or other functional groups are coupled N- or C-terminally or to any other residues (specifically or non-specifically) by means of chemical conjugation (using known organic chemistry methods).

A polypeptide according to the invention may be useful in any method which relies on affinity for IgG Fc of a reagent. Thus, the polypeptide may be used as a detection reagent, a capture reagent or a separation reagent in such methods. In particular, as already stated above, the polypeptide exhibits several characteristics which make it useful as an affinity reagent in chromatography, wherein the goal is to separate, purify and/or produce antibodies or Fc fusion proteins from a heterogeneous mixture. The polypeptide can be bound to a matrix and e.g. used for the purification of IgG Fc-containing therapeutic compounds in industrial production. Due to properties such as a high target affinity, a high stability both in acidic and basic environments and selectivity for the IgG Fc fragment over the IgG Fab fragment, the IgG Fc-binding polypeptide according to the invention is thought to present a very attractive affinity reagent.

Thus, another aspect of the present invention is a method of isolating molecules comprising IgG Fc from a liquid, which method comprises the steps:

(i) providing a liquid containing molecules comprising IgG Fc;

(ii) contacting the liquid with an IgG Fc-binding polypeptide or composition as described herein, whereby said molecules comprising IgG Fc bind to the polypeptide or composition;

(iii) isolating bound molecules comprising IgG Fc from the liquid.

In the inventive isolation method, the liquid may be derived from a culture of prokaryotic or eukaryotic, such as mammalian or plant, cells expressing molecules comprising IgG Fc, or from expression of such molecules in an alternative expression system, for example a vesicular system. Alternatively, the liquid may be derived from transgenic expression in a host, such as a plant or mammalian host.

In the context of the present invention, the terms "sample" and "liquid" may be used interchangeably. Neither term implies any limitations, for example with regard to the volume of liquid involved or other characteristics. The liquid may be of a small volume, such as an aliquot of a larger volume, e.g. for analytical purposes; or alternatively, the feed or liquid used in a large scale purification process.

In some embodiments, said molecules comprising IgG Fc are IgG molecules or fragments thereof. For example, they can be human IgG molecules or fragments thereof. In some embodiments, said molecules comprising IgG Fc are monoclonal IgG antibodies. In particular, such monoclonal IgG antibodies may be human monoclonal IgG antibodies. For example, they are human monoclonal IgG antibodies from class 1, 2 and/or 4.

In other embodiments, said molecules comprising IgG Fc are Fc fusion proteins. The Fc domain in such a fusion protein may thus, advantageously, be used as an "affinity handle" in the isolation of the fusion protein. A large variety of Fc fusion proteins have been created. For example, Fc fusion proteins having therapeutic applications include etanercept, which is a fusion between soluble TNF-α receptor and Fc, and VEGF Trap, which is a fusion between VEGF receptor domains and Fc (Holash et al, Proc Natl Acad Sci USA (2002) 99(17): 11393-11398). While these two are illustrative examples of great interest, the listing of them is non-limiting, and it is in principle possible to fuse an Fc domain to any desired protein in order to modify its properties and facilitate affinity purification thereof using the inventive IgG Fc-binding polypeptide or composition described herein as affinity ligand.

Yet another aspect of the present invention concerns a method of producing molecules comprising IgG Fc, which method comprises the steps:
(i) expressing desired molecules comprising IgG Fc;
(ii) obtaining a liquid containing molecules comprising IgG Fc from said expression;
(iii) contacting the liquid with an IgG Fc-binding polypeptide or composition as described herein, whereby molecules comprising IgG Fc bind to the polypeptide or composition;
(iv) isolating bound molecules comprising IgG Fc from the liquid, and
(v) recovering bound molecules comprising IgG Fc through elution thereof from the IgG Fc-binding polypeptide or composition.

Expression step (i) may be performed using any known expression system, for example recombinant expression in prokaryotic or eukaryotic, such as mammalian or plant, cells, or in a vesicular system. The liquid may also be derived from transgenic expression in a host, such as a plant or mammalian host.

In some embodiments, said molecules comprising IgG Fc are IgG molecules or fragments thereof. For example, they can be human IgG molecules or fragments thereof. In some embodiments, said molecules comprising IgG Fc are monoclonal IgG antibodies. In particular, such monoclonal IgG antibodies may be human monoclonal IgG antibodies. For example, they are human monoclonal IgG antibodies from class 1, 2 and/or 4.

In other embodiments, said molecules comprising IgG Fc are Fc fusion proteins.

In some embodiments of the inventive methods of isolating and producing, the IgG Fc-binding polypeptide or composition is immobilized on a matrix. In one embodiment, the present polypeptide or composition has been coupled to a matrix in the form of an insoluble carrier. Such a carrier may be one or more particles, such as beads, e.g. a chromatography resin; or irregular shapes; membranes; filters; capillaries; monoliths; and any other format commonly used in protein separation and/or purification. Thus, in general, methods that employ the polypeptides and/or compositions in accordance with the invention in vitro may be performed in different formats, such as on filters or membranes, microtitre plates, in protein arrays, on biosensor surfaces, on beads, in flow cytometry, on tissue sections, and so on. In a specific aspect, the invention provides a chromatography medium, which has an IgG Fc-binding polypeptide or composition as described herein immobilized thereon. Such a medium may be based on any known chromatography material as a matrix, and coupling of the polypeptide or composition to the matrix may be performed using any one of several known procedures.

The numbering of amino acid residues and any use of the term "position" in the sequence of the polypeptide according to the invention is relative. In a polypeptide in accordance with the invention which has as many amino acid residues as a specifically disclosed polypeptide, i.e. those described above, the positions of amino acids in the polypeptide correspond exactly to those in the disclosed polypeptides. In a situation where there is, for example, an N terminal extension compared to the disclosed polypeptides, those amino acid residues in the extended peptide that correspond to those of the non-extended peptide have the same position numbers. For example, if there is a six amino acid residue extension on the extended polypeptide, then amino acid number seven of that modified polypeptide, counting from the N terminus, corresponds to the amino acid in position number one of the disclosed polypeptide.

The invention is further illustrated by the following non-limiting examples.

EXAMPLE 1

Cleavage of a DP Dipeptide Sequence

The HER2 binding Affibody® molecule Z05494 (SEQ ID NO:8 in FIG. 1) was constructed starting from Z02891 (SEQ ID NO:7 in FIG. 1) by replacing the aspartic acid in position 37 of Z02891 to a glutamic acid. Z05494 was then used in the experiment described herein for illustrative purposes. The mutated gene was inserted into an expression vector containing the T7 promoter and encoding a hexahistidine (His$_6$) tail followed by a DP dipeptide sequence enabling acid cleavage. The expressed protein, which had the amino acid sequence SEQ ID NO:9 (FIG. 1) and was denoted His$_6$-Z05494, was harvested as a soluble product with the starting methionine removed.

After expression, the cells were lysed by heating and the soluble His$_6$-Z05494 product was purified by IMAC followed by reverse phase chromatography. The protein was aliquoted into vials in 1 mg and 5 mg portions and lyophilized.

A dilution series of 12 M, 10 M, 8 M, 6 M, 4 M, 2 M and 0.2 M was prepared for each of the following seven acids: phosphoric acid ($H_3PO_4$), acetic acid ($CH_3COOH$), formic acid ($HCOOH$), sulfuric acid ($H_2SO_4$), hydrochloric acid (HCl), nitric acid ($HNO_2$) and trifluoroacetic acid ($CF_3CO_2H$). Lyophilized His$_6$-Z05494 was diluted in de-ionized water to a final concentration of 4 mg/ml. Seven eppendorf tubes per acid, all containing 25 µl His$_6$-Z05494, were prepared. 25 µl of acid were added to the eppendorf tubes and left to incubate at 37° C. for 17 h 30 min (overnight). Acid catalyzed cleavage was stopped by increasing the pH to 7.5-8.5 by addition of different concentrations of NaOH and 125 µl 2 M Tris-HCl, pH 8. All samples were analyzed with SDS-PAGE and loaded onto an HPLC/MSD equipment.

Figure 2:
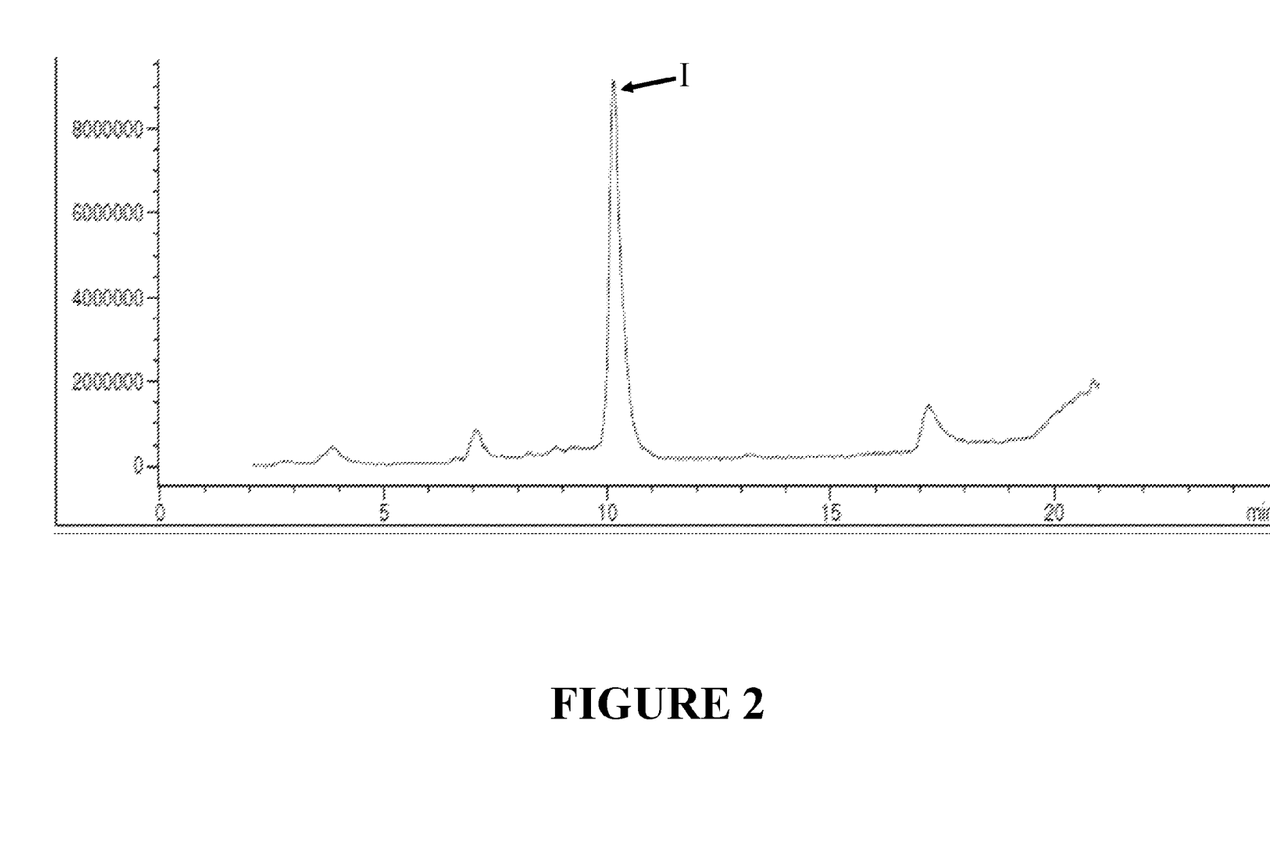
FIG. 2 is a chromatogram from HPLC/MSD analysis of a sample of His$_6$-Z05494 after treatment with 5 M phosphoric acid. The peak denoted I corresponds to cleaved (7052 Da), uncleaved (9179 Da) and modified (7268 Da) His$_6$-Z05494 molecule.

Analysis by HPLC/MSD showed that the weak acids acetic acid and formic acid cleaved a very small amount of protein at a concentration of 5-6 M, and nothing at all at lower concentrations. 5 M phosphoric acid was an exception to the results of the weak acids in general, and cleaved large amounts of the $His_6$-Z05494 molecule. FIG. 2 is a diagram from the HPLC/MSD analysis of the sample treated with 5 M phosphoric acid, and the major component is observed to be the cleaved molecule. However, small amounts of uncleaved molecules and modified cleaved molecule were also detected in the sample.

Nitric acid was too powerful for the cleavage experiment, cutting the protein irregularly. Trifluoroacetic acid did not cut the protein at the cleavage site, which led to results that were hard to interpret. Sulfuric acid and hydrochloric acid showed similar results. At lower concentrations, i.e. from around 1 to 3 M acid, the majority of the protein was cleaved. The results of the HPLC/MSD analysis confirm that the $His_6$-Z05494 molecule was cleaved, but the outcome was far from perfect and indicated that the cleavage experiments were not optimal. In almost every case, a significant amount of cleaved molecule with an extra mass of +216 Da was detected.

The results with phosphoric acid and hydrochloric acid were most favorable, and further experiments were performed with these two acids. Dilution series for HCl with the concentrations 7 M, 6 M and 4 M and for $H_3PO_4$ with the concentrations 12 M, 10 M and 8 M were made. A different buffer (2 M $NaH_2PO_4$, pH 7.4) was used to determine if the Tris buffer could have resulted in modification of the $His_6$-Z05494 molecule. The cleavage was carried out at 100° C., 80° C. and 50° C. and stopped after 1 h, 2 h, 4 h, 6 h and 8 h by increasing the pH through addition of an appropriate concentration of NaOH and 125 µl 2 M $NaH_2PO_4$, pH 7.4. The samples were analyzed on SDS-PAGE gel and loaded onto an HPLC/MSD equipment.

Figure 3:
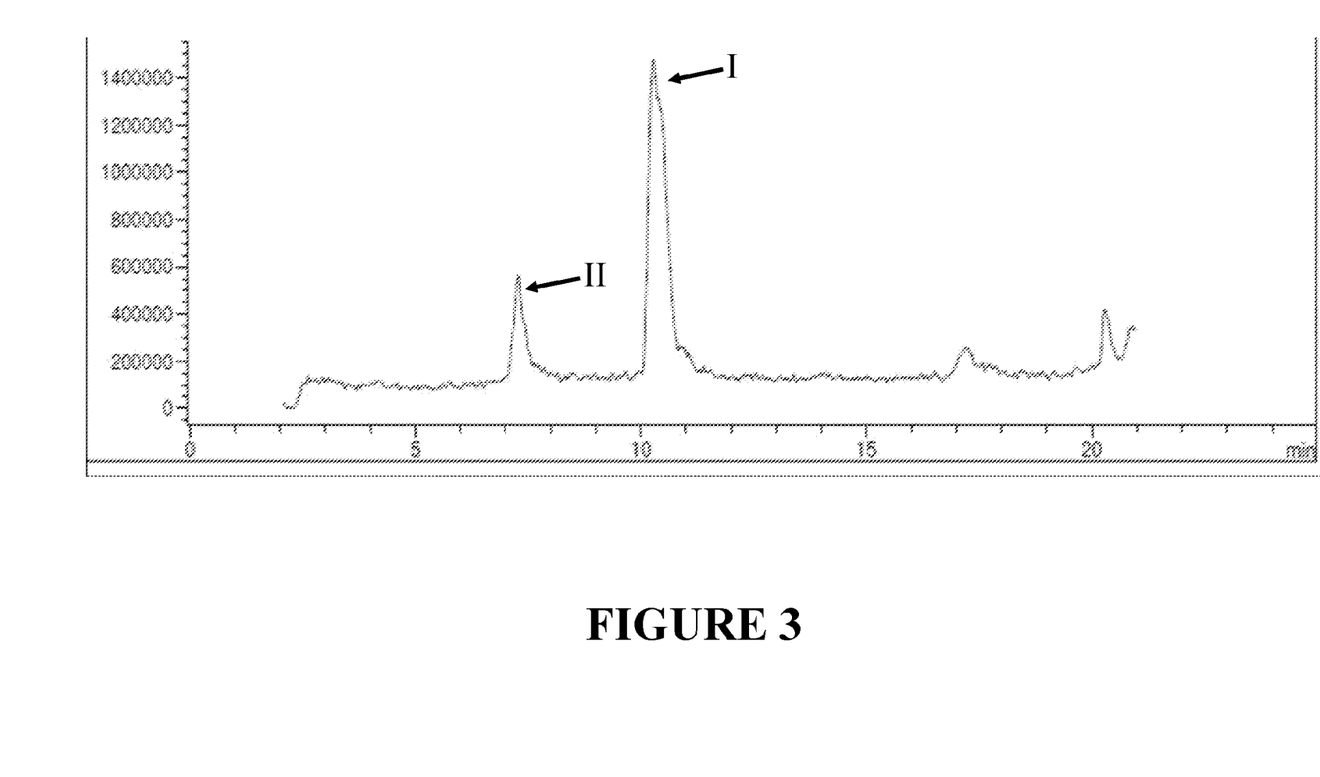
FIG. 3 is a chromatogram from HPLC/MSD analysis of a sample of His$_6$-Z05494 after treatment with 2 M hydrochloric acid for 1 h at 50° C. The peak denoted I corresponds to cleaved (7052 Da), uncleaved (9179 Da) and modified (7268 Da) His$_6$-Z05494 molecule. The peak denoted II corresponds to hexahistidyl tag (2145 Da).
Figure 4:
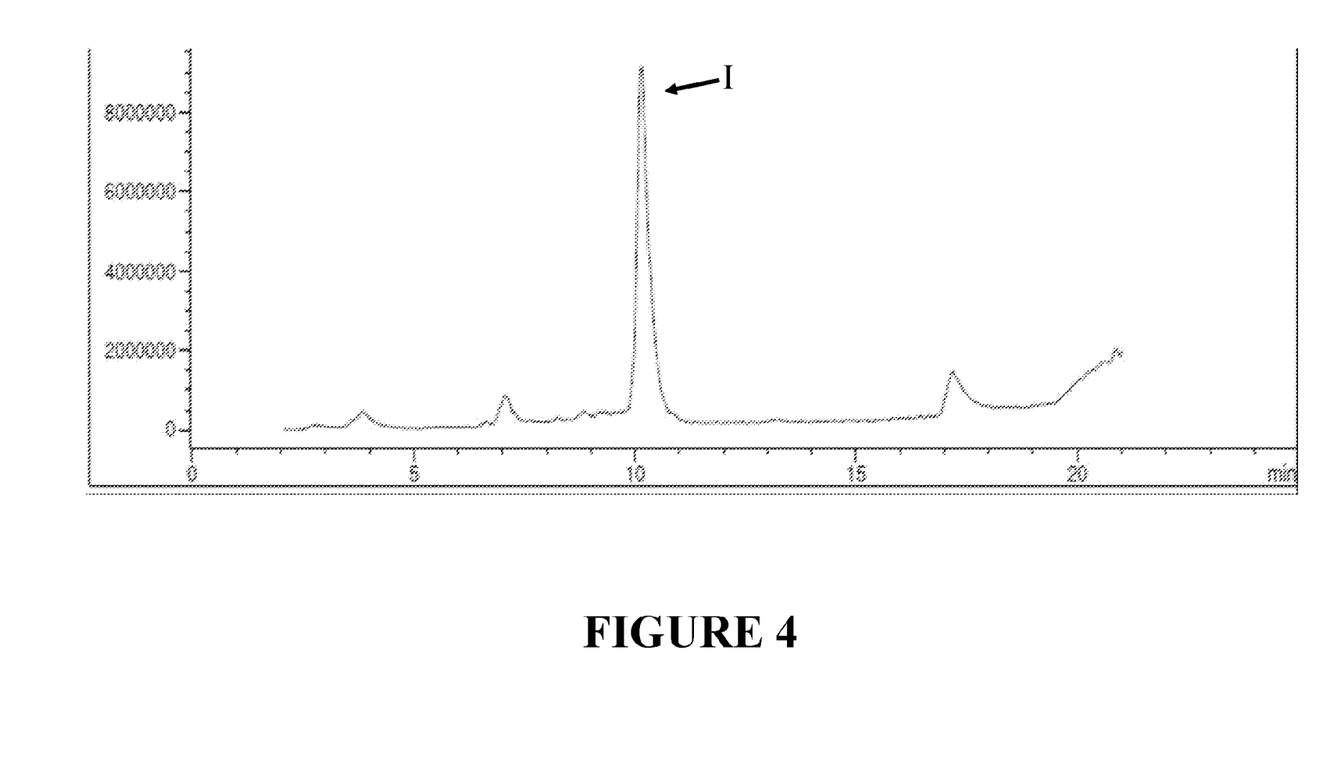
FIG. 4 is a chromatogram from HPLC/MSD analysis of a sample of His$_6$-Z05494 after treatment with 6 M phosphoric acid for 1 h at 50° C. The peak denoted I corresponds to cleaved (7052 Da) and uncleaved (9179 Da) His$_6$-Z05494 molecule.

Mass spectrometry confirmed that the temperatures 100° C. and 80° C. were clearly too high for chemical cleavage and resulted in a totally fragmented protein with both acids. The cleavage performed at 50° C. gave better results but confirmed that when a high concentration of $NaH_2PO_4$ was used as buffer, the outcome of the mass spectroscopy was affected as the phosphate precipitated. The high concentration of phosphate in the samples led to a high degree of modifications on the cleaved $His_6$-Z05494 molecule with an extra mass of +79 Da. Cleaved $His_6$-Z05494 molecule with a mass of 7269 Da, that is an extra mass of +216 Da, was also detected. The best cleavage results with hydrochloric acid were achieved with the concentration 2 M and 3 M for 1-3 h. With phosphoric acid, the best cleavage was accomplished using 5-6 M acid for 1-4 h. FIGS. 3 and 4 illustrate diagrams for the best results with hydrochloric acid and phosphoric acid, respectively.

To summarize, the experiments described above show that the DP dipeptide may be successfully cleaved using acid catalyzed hydrolysis, when this dipeptide sequence is present in a spacer preceding a three-helix bundle protein domain, such as the three-helix bundle IgG Fc-binding domain present in the polypeptide according to the invention.

EXAMPLE 2

Design Considerations in the Preparation of an IgG Fc-binding Composition According to the Invention A pilot experiment is performed in order to assess the optimal length of a polymer linker in an IgG Fc-binding composition according to the invention, with a view to binding two monoclonal antibodies (mAbs) with two IgG Fc-binding polypeptides wherein n=1, i.e. two single domains, coupled "tail-to-tail" via their respective $C_{CTERM-1}$ residues onto a poly(ethylene glycol) (PEG) linker. The optimal linker is sufficiently long to enable binding of two mAbs without steric interference, but not long enough to allow both IgG Fc-binding domains to bind the same mAb. Homobifunctional, thiol reactive PEG (Bis-maleimide-dPEG) may be purchased from Quanta Biodesign Ltd. The catalogue contains variants having either 3 or 11 ethylene glycol units, but other alternatives are available upon request. A linker of suitable length has been found when the two IgG Fc-binding domains connected by a PEG do not have a preference for binding to the same antibody, but bind to two separate antibodies. Thereby, networks of antibodies and PEG-conjugated IgG Fc-binding domains are enabled.

The optimization experiment preferably starts with an evaluation of the two commercially available linker lengths, and then continues with linkers of intermediate lengths, or with a length of more than 11 ethylene glycol units. The tail-to-tail orientation of the two IgG Fc-binding polypeptides allows separation of the domains by rotation around the same "axis", and hence provides a larger distance between the binding surfaces, compared to a situation wherein there is a "head-to-tail" orientation using a spacer of the same lengths. A "head-to-tail" orientation typically results from recombinant expression of several IgG Fc-binding domains in series, as a multimeric fusion protein separated by peptidic spacers.

An experiment aiming to assess that networks of binding polypeptides and mAbs are obtained is performed using a human IgG1 antibody (or a mixture of human IgG1 antibodies). Following incubation of IgG Fc-binding composition with mAbs under suitable conditions, any complexes formed are analyzed using size exclusion chromatography (SEC), and the result is confirmed by high-molecular weight mass spectrometry analysis. In the SEC experiment, the sizes of the complexes formed are determined by comparison with a size reference standard. Starting from a linker length that yields primarily networks and complexes larger than 1:1 (referring to complexes of one PEG-linked dimer of IgG-binding domains and one IgG molecule), the amount of 1:1 complexes formed with a successively reduced linker length is investigated. The optimal length PEG contains one or two ethylene glycol units less than the length showing a clear increase in the amount of 1:1 complex found. Preferably, a PEG molecule having two units less is used, if this does not result in an increase in 1:1 complex content compared with a molecule having one less ethylene glycol unit. Below a certain length, the linker will be too short to allow network formation.

A second optimization experiment is then performed to assess the optimal length for allowing a trimer (i.e. three monomeric IgG Fc-binding polypeptide domains coupled equidistantly on the same PEG chain) to bind three separate mAbs. The same is then done with a tetramer, investigating binding of four mAbs.

As described in the general section above, the composition according to the invention is suitably connectable to a matrix or chromatography medium. In order to find the optimal length of the polymer linker connecting the composition to the matrix, the starting point is to investigate a linker which is at least as long as the linker between IgG Fc-binding domains.

Furthermore, the chemical nature of the group used for attachment to the matrix is preferably different from the maleimide used for conjugation of the IgG Fc-binding domains to the linker polymer. Activation of a reacting group may be done either by base or acid, due to the stability of the polypeptide domain against both conditions. As non-limiting examples of chemistries that may be suitable, Quanta Biodesign Ltd makes PEG having a t-butyl ester as well as tosylate-derivatives that may be activated and used for proprietary chemistry, and azido-PEG that may be used in click-chemistry reactions. Additional alternatives are well known in the art.

What is claimed is:

1. An immunoglobulin G Fc region binding polypeptide, comprising an mamino acid sequence:

```
i) X₁-([spacer1]-(SEQ ID NO: 10)-X₁₇LPX₂₀-
   (SEQ ID NO: 11)-X₃₆-(SEQ ID NO: 12)-
   X₅₁-(SEQ ID NO: 13)-[spacer2])ₙ-C_{CTERM-1}X_{CTERM}
``` wherein, independently of each other,
$X_1$ is P or nothing;
[spacer1] is an amino acid sequence consisting of 1-3 amino acid residues;
$X_{17}$ is any amino acid residue;
$X_{20}$ is any amino acid residue;
$X_{36}$ is any amino acid residue except for D;
$X_{51}$ is any amino acid residue;
[spacer2] is an amino acid sequence consisting of 0-20 amino acid residues;
$X_{CTERM}$ is D or nothing;
and n is 1-4.

2. The IgG Fc-binding polypeptide of claim 1, wherein [spacer1] is selected from A, AE and AEA.

3. The IgG Fc-binding polypeptide of claim 2, wherein [spacer1] is A.

4. The IgG Fc-binding polypeptide of claim 1, wherein $X_{17}$ is H.

5. The IgG Fc-binding polypeptide of claim 1, wherein $X_{20}$ is any amino acid residue except for N, for example T.

6. The IgG Fc-binding polypeptide of claim 1, wherein $X_{20}$ is N.

7. The IgG Fc-binding polypeptide of claim 1, wherein $X_{36}$ is selected from E and A.

8. The IgG Fc-binding polypeptide of claim 1, wherein $X_{51}$ is any amino acid residue except for N.

9. The IgG Fc-binding polypeptide of claim 1, wherein $X_{51}$ is N.

10. The IgG Fc-binding polypeptide of claim 1, wherein all amino acid residues of [spacer2] are independently selected from A, E, F, G, I, K, L, P, Q, R, S, T and V.

11. The IgG Fc-binding polypeptide of claim 1, wherein [spacer2] is G.

12. The IgG Fc-binding polypeptide of claim 1, wherein n is 1.

13. The IgG Fc-binding polypeptide of claim 1, wherein n is 2.

14. The IgG Fc-binding polypeptide of claim 1, wherein n is 4.

15. The IgG Fc-binding polypeptide of claim 1, which binds to IgG Fc such that the $K_D$ value of the interaction is at most $1 \times 10^{-6}$ M.

16. The IgG Fc-binding polypeptide of claim 15, which binds to IgG Fc such that the $K_D$ value of the interaction is at most $1 \times 10^{-7}$ M.

17. The IgG Fc-binding polypeptide of claim 16, which binds to IgG Fc such that the $K_D$ value of the interaction is at most $5 \times 10^{-8}$ M.

18. The IgG Fc-binding polypeptide of claim 1, which is capable of binding to the Fc portion of a human IgG molecule.

19. The IgG Fc-binding polypeptide of claim 18, which is capable of binding to classes 1, 2 and 4 of human IgG.

20. The IgG Fc-binding polypeptide of claim 1, which is capable of binding to the interface between the CH2 and CH3 domains of IgG Fc.

21. The IgG Fc-binding polypeptide an amino acid sequence selected from SEQ ID NO:5-6.

22. The IgG Fc-binding polypeptide of claim 1, in which $X_1$ is P and $X_{CTERM}$ is D.

23. An IgG Fc-binding polypeptide comprising an amino acid sequence selected from SEQ ID NO:1-4.

24. A polynucleotide comprising a nucleotide sequence encoding the polypeptide of claim 1.

25. A multimer polypeptide comprising:
at least two subunits, each subunit being the polypeptide of claim 22; and
an N-terminal leader peptide comprising a D residue as the last residue thereof.

26. A polynucleotide comprising the nucleotide sequence encoding a multimer polypeptide of claim 25.

* * * * *

```
                        SEQUENCE LISTING

<160> NUMBER OF SEQ ID NOS: 13

<210> SEQ ID NO 1
<211> LENGTH: 58
<212> TYPE: PRT
<213> ORGANISM: Artificial Sequence
<220> FEATURE:
<223> OTHER INFORMATION: Synthetic Peptide

<400> SEQUENCE: 1

Pro Ala Lys Phe Asp Lys Glu Gln Gln Asn Ala Phe Tyr Glu Ile Leu
1               5                   10                  15

His Leu Pro Asn Leu Thr Glu Glu Gln Arg Asn Ala Phe Ile Gln Lys
            20                  25                  30

Leu Lys Asp Glu Pro Ser Gln Ser Ala Glu Leu Leu Ala Glu Ala Lys
        35                  40                  45

Gln Leu Asn Glu Ala Gln Ala Gly Cys Asp
    50                  55

<210> SEQ ID NO 2
<211> LENGTH: 58
<212> TYPE: PRT
<213> ORGANISM: Artificial Sequence
<220> FEATURE:
<223> OTHER INFORMATION: Synthetic Peptide

<400> SEQUENCE: 2

Pro Ala Lys Phe Asp Lys Glu Gln Gln Asn Ala Phe Tyr Glu Ile Leu
1               5                   10                  15

His Leu Pro Thr Leu Thr Glu Glu Gln Arg Asn Ala Phe Ile Gln Lys
            20                  25                  30

Leu Lys Asp Glu Pro Ser Gln Ser Ala Glu Leu Leu Ala Glu Ala Lys
        35                  40                  45

Gln Leu Asp Glu Ala Gln Ala Gly Cys Asp
    50                  55

<210> SEQ ID NO 3
<211> LENGTH: 116
<212> TYPE: PRT
<213> ORGANISM: Artificial Sequence
<220> FEATURE:
<223> OTHER INFORMATION: Synthetic Peptide

<400> SEQUENCE: 3

Pro Ala Lys Phe Asp Lys Glu Gln Gln Asn Ala Phe Tyr Glu Ile Leu
1               5                   10                  15

His Leu Pro Asn Leu Thr Glu Glu Gln Arg Asn Ala Phe Ile Gln Lys
            20                  25                  30

Leu Lys Asp Glu Pro Ser Gln Ser Ala Glu Leu Leu Ala Glu Ala Lys
        35                  40                  45

Gln Leu Asn Glu Ala Gln Ala Pro Lys Ala Glu Ala Lys Phe Asp Lys
    50                  55                  60

Glu Gln Gln Asn Ala Phe Tyr Glu Ile Leu His Leu Pro Asn Leu Thr
65                  70                  75                  80

Glu Glu Gln Arg Asn Ala Phe Ile Gln Lys Leu Lys Asp Glu Pro Ser
                85                  90                  95
```

Gln Ser Ala Glu Leu Leu Ala Glu Ala Lys Gln Leu Asn Glu Ala Gln
                100                 105                 110

Ala Gly Cys Asp
        115

<210> SEQ ID NO 4
<211> LENGTH: 116
<212> TYPE: PRT
<213> ORGANISM: Artificial Sequence
<220> FEATURE:
<223> OTHER INFORMATION: Synthetic Peptide

<400> SEQUENCE: 4

Pro Ala Lys Phe Asp Lys Glu Gln Gln Asn Ala Phe Tyr Glu Ile Leu
1               5                   10                  15

His Leu Pro Thr Leu Thr Glu Glu Gln Arg Asn Ala Phe Ile Gln Lys
                20                  25                  30

Leu Lys Asp Glu Pro Ser Gln Ser Ala Glu Leu Leu Ala Glu Ala Lys
            35                  40                  45

Gln Leu Asp Glu Ala Gln Ala Pro Lys Ala Glu Ala Lys Phe Asp Lys
        50                  55                  60

Glu Gln Gln Asn Ala Phe Tyr Glu Ile Leu His Leu Pro Thr Leu Thr
65                  70                  75                  80

Glu Glu Gln Arg Asn Ala Phe Ile Gln Lys Leu Lys Asp Glu Pro Ser
                85                  90                  95

Gln Ser Ala Glu Leu Leu Ala Glu Ala Lys Gln Leu Asp Glu Ala Gln
                100                 105                 110

Ala Gly Cys Asp
        115

<210> SEQ ID NO 5
<211> LENGTH: 116
<212> TYPE: PRT
<213> ORGANISM: Artificial Sequence
<220> FEATURE:
<223> OTHER INFORMATION: Synthetic Peptide

<400> SEQUENCE: 5

Ala Glu Ala Lys Phe Asp Lys Glu Gln Gln Asn Ala Phe Tyr Glu Ile
1               5                   10                  15

Leu His Leu Pro Asn Leu Thr Glu Glu Gln Arg Asn Ala Phe Ile Gln
                20                  25                  30

Lys Leu Lys Asp Glu Pro Ser Gln Ser Ala Glu Leu Leu Ala Glu Ala
            35                  40                  45

Lys Gln Leu Asn Glu Ala Gln Ala Pro Lys Ala Glu Ala Lys Phe Asp
        50                  55                  60

Lys Glu Gln Gln Asn Ala Phe Tyr Glu Ile Leu His Leu Pro Asn Leu
65                  70                  75                  80

Thr Glu Glu Gln Arg Asn Ala Phe Ile Gln Lys Leu Lys Asp Glu Pro
                85                  90                  95

Ser Gln Ser Ala Glu Leu Leu Ala Glu Ala Lys Gln Leu Asn Glu Ala
                100                 105                 110

Gln Ala Gly Cys
        115

<210> SEQ ID NO 6
<211> LENGTH: 116
<212> TYPE: PRT
<213> ORGANISM: Artificial Sequence

```
<220> FEATURE:
<223> OTHER INFORMATION: Synthetic Peptide

<400> SEQUENCE: 6

Ala Glu Ala Lys Phe Asp Lys Glu Gln Gln Asn Ala Phe Tyr Glu Ile
1               5                   10                  15

Leu His Leu Pro Thr Leu Thr Glu Glu Gln Arg Asn Ala Phe Ile Gln
                20                  25                  30

Lys Leu Lys Asp Glu Pro Ser Gln Ser Ala Glu Leu Leu Ala Glu Ala
            35                  40                  45

Lys Gln Leu Asp Glu Ala Gln Ala Pro Lys Ala Glu Ala Lys Phe Asp
    50                  55                  60

Lys Glu Gln Gln Asn Ala Phe Tyr Glu Ile Leu His Leu Pro Thr Leu
65                  70                  75                  80

Thr Glu Glu Gln Arg Asn Ala Phe Ile Gln Lys Leu Lys Asp Glu Pro
                85                  90                  95

Ser Gln Ser Ala Glu Leu Leu Ala Glu Ala Lys Gln Leu Asp Glu Ala
            100                 105                 110

Gln Ala Gly Cys
        115

<210> SEQ ID NO 7
<211> LENGTH: 58
<212> TYPE: PRT
<213> ORGANISM: Artificial Sequence
<220> FEATURE:
<223> OTHER INFORMATION: Synthetic Peptide

<400> SEQUENCE: 7

Val Asp Ala Lys Tyr Ala Lys Glu Met Arg Asn Ala Tyr Trp Glu Ile
1               5                   10                  15

Ala Leu Leu Pro Asn Leu Thr Asn Gln Gln Lys Arg Ala Phe Ile Arg
                20                  25                  30

Lys Leu Tyr Asp Asp Pro Ser Gln Ser Ser Glu Leu Leu Ser Glu Ala
            35                  40                  45

Lys Lys Leu Asn Asp Ser Gln Ala Pro Lys
    50                  55

<210> SEQ ID NO 8
<211> LENGTH: 58
<212> TYPE: PRT
<213> ORGANISM: Artificial Sequence
<220> FEATURE:
<223> OTHER INFORMATION: Synthetic Peptide

<400> SEQUENCE: 8

Val Asp Ala Lys Tyr Ala Lys Glu Met Arg Asn Ala Tyr Trp Glu Ile
1               5                   10                  15

Ala Leu Leu Pro Asn Leu Thr Asn Gln Gln Lys Arg Ala Phe Ile Arg
                20                  25                  30

Lys Leu Tyr Asp Glu Pro Ser Gln Ser Ser Glu Leu Leu Ser Glu Ala
            35                  40                  45

Lys Lys Leu Asn Asp Ser Gln Ala Pro Lys
    50                  55

<210> SEQ ID NO 9
<211> LENGTH: 81
<212> TYPE: PRT
<213> ORGANISM: Artificial Sequence
<220> FEATURE:
```

```
<223> OTHER INFORMATION: Synthetic Peptide

<400> SEQUENCE: 9

Gly Ser Ser His His His His His His Leu Gln Ser Ser Gly Val Asp
1               5                   10                  15

Leu Gly Thr Asp Pro Val Asp Ala Lys Tyr Ala Lys Glu Met Arg Asn
            20                  25                  30

Ala Tyr Trp Glu Ile Ala Leu Leu Pro Asn Leu Thr Asn Gln Gln Lys
        35                  40                  45

Arg Ala Phe Ile Arg Lys Leu Tyr Asp Glu Pro Ser Gln Ser Ser Glu
    50                  55                  60

Leu Leu Ser Glu Ala Lys Lys Leu Asn Asp Ser Gln Ala Pro Lys Val
65                  70                  75                  80

Asp

<210> SEQ ID NO 10
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 10

Lys Phe Asp Lys Glu Gln Gln Asn Ala Phe Tyr Glu Ile Leu
1               5                   10

<210> SEQ ID NO 11
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 11

Leu Thr Glu Glu Gln Arg Asn Ala Phe Ile Gln Lys Leu Lys Asp
1               5                   10                  15

<210> SEQ ID NO 12
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 12

Pro Ser Gln Ser Ala Glu Leu Leu Ala Glu Ala Lys Gln Leu
1               5                   10

<210> SEQ ID NO 13
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 13

Glu Ala Gln Ala
1
```